(12) United States Patent
Talutis

(10) Patent No.: US 7,024,956 B2
(45) Date of Patent: Apr. 11, 2006

(54) SENSOR BALL VALVE SAFETY INTERLOCK

(75) Inventor: Stephen B. Talutis, Milton, MA (US)

(73) Assignee: Invensys Systems, Inc., Foxboro, MA (US)

( * ) Notice: Subject to any disclaimer, the term of this patent is extended or adjusted under 35 U.S.C. 154(b) by 172 days.

(21) Appl. No.: 10/742,470

(22) Filed: Dec. 18, 2003

(65) Prior Publication Data
US 2005/0132825 A1 Jun. 23, 2005

(51) Int. Cl.
G01N 1/00 (2006.01)

(52) U.S. Cl. .................................... 73/866.5
(58) Field of Classification Search ............. 73/866.5, 73/863.85; 374/148, 208; 251/149.9
See application file for complete search history.

(56) References Cited

U.S. PATENT DOCUMENTS 4,598,581 A * 7/1986 Brekke ...................... 73/117.3
6,360,619 B1 * 3/2002 Schultz, Jr. .............. 73/863.86

OTHER PUBLICATIONS

Instruction Book 3569; PH10 DolpHin Series pH Sensors and ORP10 DolpHin Series ORP Sensors; Sep. 6, 2002.

* cited by examiner

Primary Examiner—Robert Raevis
(74) Attorney, Agent, or Firm—David Barron, Esq.; Richard L. Sampson, Esq.

(57) ABSTRACT

An interlocked valve sensor insertion assembly for use in a manufacturing process is shown and described. The assembly includes a ball valve configured to alternately couple and decouple a retraction chamber with the process. An insertion assembly is coupled to the retraction chamber, and includes an axially slidable insertion tube with a sensor supported on one end. The tube has a range of motion capable of extending the sensor into the valve. A fastener releasably couples the tube to the insertion assembly, and an actuator is configured for engagement with both the valve and the fastener. The actuator is configured to alternately engage and disengage the fastener when the valve is respectively disposed in open and closed positions.

23 Claims, 3 Drawing Sheets

SENSOR BALL VALVE SAFETY INTERLOCK

BACKGROUND

1. Technical Field

This invention relates to factory automation equipment, and more particularly to an improved ball valve insertion assembly having a safety interlock for enabling safe withdrawal of a sensor from a process fluid without requiring cessation of process fluid flow.

2. Background Information

Throughout this application, various publications, patents and published patent applications are referred to by an identifying citation. The disclosures of the publications, patents and published patent applications referenced in this application are hereby incorporated by reference into the present disclosure.

Sensors of various types are routinely used in factory automation systems to measure parameters of process fluid flow. For example, DolpHin™ Series pH or ORP (Oxidation-Reduction Potential) sensors (Foxboro® Company of Foxboro, Mass.) or any number of other conventional sensors, such as conductivity and resistivity sensors, are often used to track and manage the quality of fluid flow in facilities ranging from petroleum refineries to pharmaceutical and chemical processing facilities.

These processes tend to involve highly complex systems of fluid flow, which may be particularly difficult and expensive to start and stop. Indeed, considerable effort is expended to ensure continuous operation of such processes, since even relatively short periods of operational downtime may represent tens, or even hundreds of thousands of dollars of lost revenue. Accordingly, a desirable capability is that of removing sensors for servicing, e.g., calibration, cleaning, or replacement, without having to terminate the process flow.

Ball valve insertion (BVI) assemblies have been developed and widely used to provide this capability. BVI assemblies serve as ports through which the sensors may be conveniently inserted into the process flow, and subsequently withdrawn therefrom in a three-step operation which includes retracting the sensor from the flow, isolating the assembly from the process, and then physically removing the sensor from the assembly, e.g., for servicing or replacement. A shut-off valve is generally used to isolate the assembly. Accordingly, this approach enables one to service and replace sensors without any process downtime.

While these BVI assemblies represent a significant improvement over prior approaches, there is room for improvement. As with any process penetration, leaks sometimes occur. Moreover, in spite of adequate instructions and warning labels, users may incorrectly execute the three-step sensor removal process, and inadvertently attempt to withdraw and remove a sensor without first closing the ball valve to isolate the sensor from the process flow. Such a failure may result in a fluid release.

While in some instances a fluid release may be relatively benign, in other instances, such as in the event the process fluid is caustic or hazardous, a release may be particularly undesirable, potentially necessitating costly cleanup and reporting efforts.

Thus, a need exists for an improved ball valve insertion assembly that effectively prevents a sensor from being retracted and removed prior to actuation of the ball valve.

SUMMARY

One aspect of the present invention includes an interlocked ball valve sensor insertion assembly for use in a manufacturing process. The assembly includes a ball valve configured to alternately couple and decouple a retraction chamber with the process. An insertion assembly is coupled to the retraction chamber, and includes an axially slidable insertion tube with a sensor supported on an end thereof. The tube has a range of motion extending from an insertion position to a retraction position. The sensor extends into the ball valve and into operative engagement with the process when in the insertion position, and is located on the opposite side of the ball valve from the process when in the retraction position. A first fastener is coupled to the tube, and selectively permits and prevents movement of the tube. A second fastener is coupled to the tube, and selectively permits and prevents removal of the tube from the insertion assembly. An actuator operates the ball valve, while also alternately engaging and disengaging the second fastener for respectively inhibiting and enabling access to the second fastener. The actuator thus couples the process fluid with the retraction chamber and simultaneously inhibits operational access to the second fastener when the tube is in the insertion position. The actuator also decouples the process fluid from the retraction chamber and simultaneously enables operational access to the fastener when the tube is in the retracted position.

Another aspect of the invention includes an interlocked valve sensor insertion assembly for use in a manufacturing process. The assembly includes a ball valve configured to alternately couple and decouple a retraction chamber with the process. An insertion assembly is coupled to the retraction chamber, and includes an axially slidable insertion tube with a sensor supported on one end. The tube has a range of motion capable of extending the sensor into the valve. A fastener releasably couples the tube to the insertion assembly, and an actuator is configured for engagement with both the valve and the fastener. The actuator alternately engages and disengages the fastener when the valve is respectively disposed in open and closed positions.

A further aspect of the invention includes a method of providing an interlocked valve sensor insertion assembly for use with a manufacturing process. The method includes providing a valve couplable with the manufacturing process, the valve having a range of motion extending from an open position to a closed position; coupling a retraction chamber to the valve; and coupling an insertion assembly to the retraction chamber. The method also includes providing the insertion assembly with an axially slidable insertion tube; configuring an end of the insertion tube to support a sensor; and configuring the insertion tube with a range of motion extending from an insertion position to a retraction position, so that the sensor extends into the valve when in the insertion position. A fastener is used to releasably couple the tube to the insertion assembly; and an actuator is configured for selective engagement with both the valve and the fastener, so that the actuator alternately moves the valve between open and closed positions while respectively engaging and disengaging the fastener.

BRIEF DESCRIPTION OF THE DRAWINGS

The above and other features and advantages of this invention will be more readily apparent from a reading of the following detailed description of various aspects of the invention taken in conjunction with the accompanying drawings, in which.

DETAILED DESCRIPTION

Figure 1:
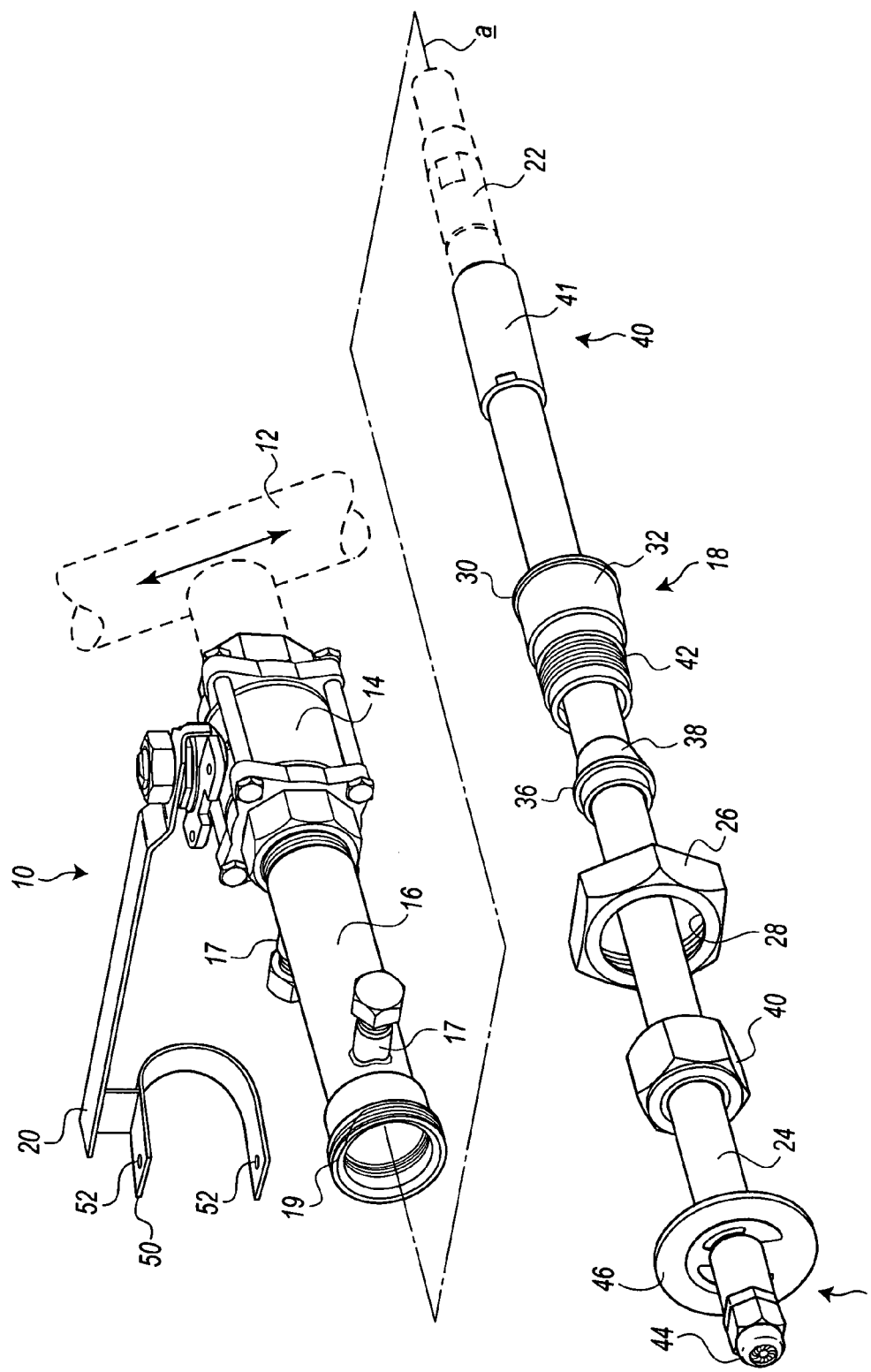
FIG. 1 is an exploded perspective view of a ball valve insertion assembly of the present invention, with a portion of a typical operational environment shown in phantom.

In the following detailed description, reference is made to the accompanying drawings that form a part hereof, and in which is shown by way of illustration, specific embodiments in which the invention may be practiced. These embodiments are described in sufficient detail to enable those skilled in the art to practice the invention, and it is to be understood that other embodiments may be utilized. It is also to be understood that structural, procedural and system changes may be made without departing from the spirit and scope of the present invention. The following detailed description is, therefore, not to be taken in a limiting sense, and the scope of the present invention is defined by the appended claims and their equivalents. For clarity of exposition, like features shown in the accompanying drawings shall be indicated with like reference numerals and similar features as shown in alternate embodiments in the drawings shall be indicated with similar reference numerals.

Briefly described, as shown in the figures, an embodiment of the present invention includes an interlocked ball valve sensor insertion assembly 10 used in connection with a manufacturing process 12 (shown in phantom). Assembly 10 includes a ball valve 14 coupled to an insertion assembly 18. An interlock 20 coupled to ball valve 14 is alternately engagable with insertion assembly 18 to nominally prevent removal of a sensor 22 when the valve 14 is open.

Advantageously, this embodiment helps ensure that the user effects the sensor removal steps in the required order. This, in turn, helps prevent the inadvertent release of fluid from process 12 that may otherwise occur during attempted sensor removal without first closing ball valve 14.

Where used in this disclosure, the term "axial" refers to a direction relative to the assembled embodiment(s) described herein, which is substantially parallel to axis a of insertion tube 24. The term "downstream" refers to a direction parallel to the axial direction, directed towards process 12 when the embodiment(s) is coupled to the process.

Figure 2:
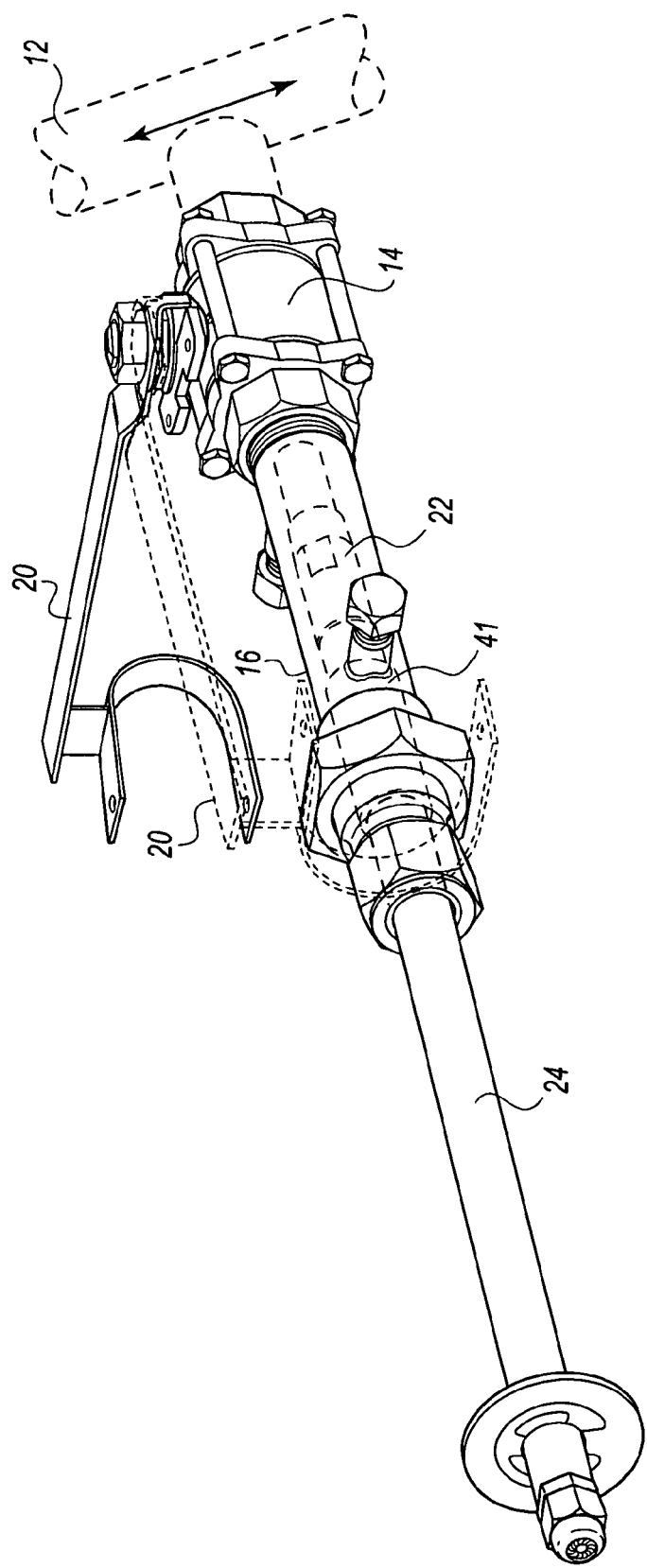
FIG. 2 is elevational side view of the ball valve insertion assembly of FIG. 1, with portions shown in phantom to represent movement, and with an insertion tube thereof shown in its retracted position.
Figure 3:
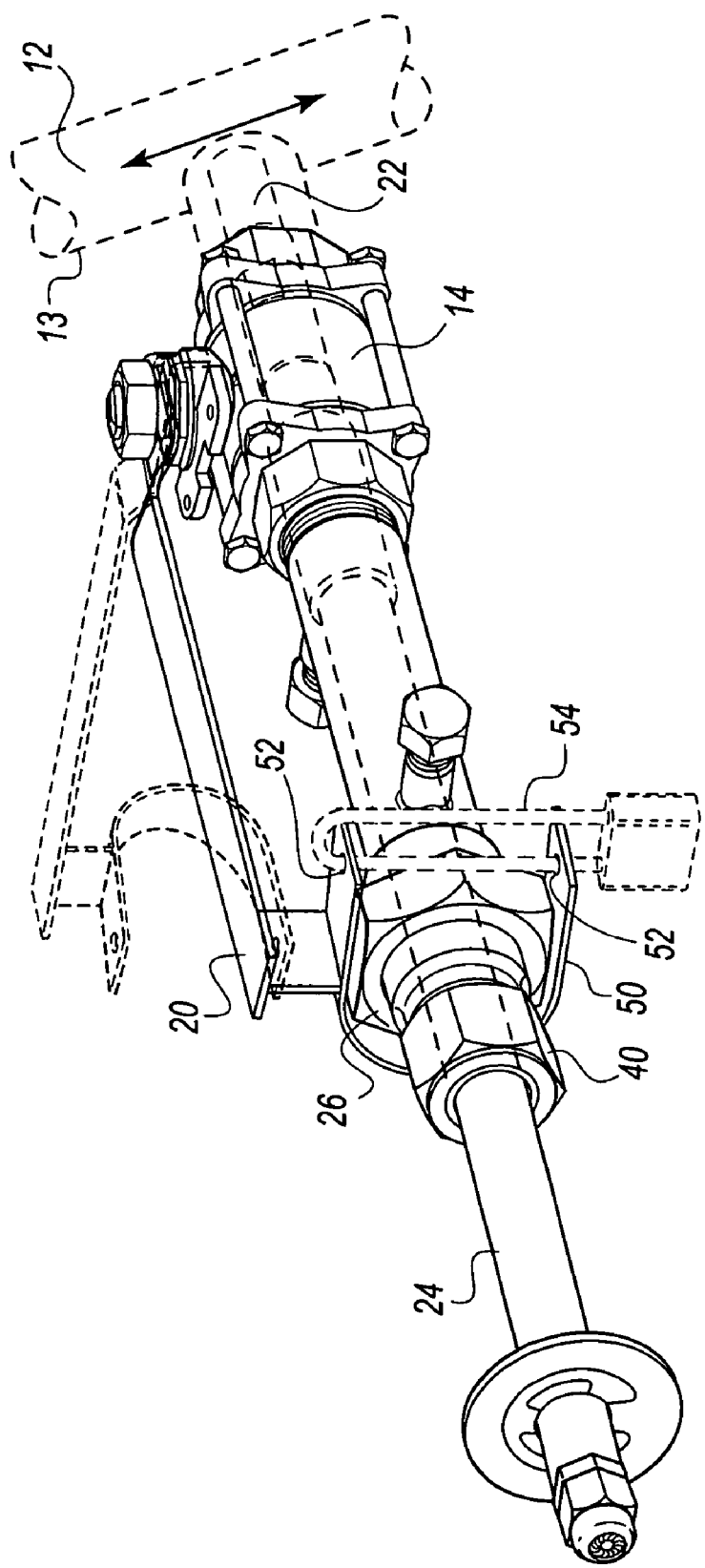
FIG. 3 is a view similar to that of FIG. 2, with the insertion tube thereof shown in its inserted position.

Referring now to FIGS. 1–3, embodiments of the present invention will be more thoroughly described. Turning to FIG. 1, valve sensor insertion assembly 10 may be used to couple a sensor 22 to a manufacturing process 12 (shown in phantom). In particular embodiments, assembly 10 includes a valve (e.g., a ball valve) 14 coupled on a downstream side thereof to process 12. An upstream side of valve 14 is coupled to a retraction chamber 16. Ball valve 14 is thus configured to alternately couple and decouple retraction chamber 16 with process 12, as will be discussed in greater detail below.

As also shown, retraction chamber 16 may include conventional purge ports 17, which are usable in a conventional manner to remove process fluid from chamber 16 prior to withdrawal (i.e., removal) of sensor 22 for replacement or servicing. Use of the retraction chamber, including ports 17, will be discussed in greater detail below with respect to the operation of embodiments of the present invention.

In the embodiment shown, retraction chamber 16 is provided with a fastener, i.e., fastening means, which includes a series of threads 19 at its upstream end, sized for threaded engagement with a fastener (chamber nut) 26 of insertion assembly 18. Chamber nut 26 includes a shoulder 28 sized and shaped to engage flange 30 of a coupling 32. In this manner, as the nut is threadably engaged with threads 19, flange 30 is captured and secured between nut 26 and threads 19. This configuration effectively fastens insertion assembly 18 to the upstream end of retraction chamber 16.

Insertion assembly 18 also includes an insertion tube 24 sized and shaped for slidable receipt within coupling 32. A pressure fitting (i.e., fitting means) is provided, which in the embodiment shown, includes a pressure washer 36 having a generally downstream oriented frusto-conical surface 38, and a suitable fastener (tubing nut) 40. Nut 40 is sized and shaped to threadably engage threads 42 of coupling 32, while capturing washer 36 therebetween in a manner substantially similar to that of coupling 32 described above.

Surface 38 of washer 36 is sized in a manner common to conventional pressure fittings, i.e., with an outer diameter ranging from less than, to greater than, the inner diameter of coupling 32. Such a configuration serves to apply a progressively greater radially compressive force onto tube 24 as tubing nut 40 is tightened onto coupling 32. Tubing nut 40 may thus be loosened to permit tube 24 to be moved within its axial range of motion, and tightened to secure tube 24 in position, as discussed below.

Tube 24 includes a distal sensor end 40, having a sensor sleeve 41 disposed thereon, which is configured to support sensor 22 (shown in phantom) in any suitable manner, e.g., with mating threads. As mentioned above, sensor 22 may include nominally any conventional sensor, including those configured to measure pH, ORP, or any number of commonly measured analytes.

Proximal end 42 of tube 24 includes a cable fitting 44 which may be used to electrically couple electrical leads of sensor 22 (extending axially within tube 24) to suitable instrumentation, such as to a conventional process variable transmitter (not shown). Proximal end 42 may also optionally include a push/pull plate 46 to facilitate axial movement of tube 24.

An actuator 20, is coupled at a proximal end to ball valve 14. In the embodiment shown, actuator 20 is configured in the form of a handle which is manually operable to alternately open and close ball valve 14 in a conventional manner. For example, in FIG. 2, actuator 20 is shown in the closed position, and is shown in phantom in the open position. Actuator 20 thus operates ball valve 14 to alternately couple and decouple retraction chamber 16 with process 12.

Although a manually operated actuator 20 is shown, the actuator may include any number of commonly available electronically operated devices, which may be operated either automatically, or by user input.

At its distal end, actuator 20 includes a guard 50 sized and shaped for operative engagement with fastener 26. As shown in FIG. 3 (and in FIG. 2 in phantom), this operative engagement includes placing guard 50 in superposition with at least a portion of the peripheral surface of fastener (chamber nut) 26.

For example, in the embodiment shown, the guard includes a U-shaped member having opposed, parallel ends configured for superposition with opposed parallel surfaces of chamber nut 26.

Such superposition effectively inhibits operational access to the fastener, e.g., by nominally preventing a user from applying a wrench to, and loosening, chamber nut 26 when actuator 20 is disposed in the (valve) open position shown in FIG. 3. Moreover, in an alternate embodiment, a holes 52 (shown in phantom) may extend through one or both ends of the U-shaped guard 50. An additional lockout mechanism (e.g., a padlock 54) may be extended through one or both holes 52 when actuator 20 is disposed in the open position as shown in FIG. 3, to help further ensure that chamber nut 26 is not accidentally loosened prior to closure of valve 14.

When actuator 20 is disposed in the (valve) closed position (FIGS. 1 and 2), i.e., after removing padlock 54 if so equipped, guard 50 moves out of operative engagement with the chamber nut, to enable a user to gain access sufficient to enable nut 26 to be loosened for withdrawal of the tube from the insertion assembly.

Turning now to FIGS. 2 and 3, tube 24 is movable within an axial range of motion extending from a retraction position (FIG. 2) to an insertion position (FIG. 3). As shown in FIG. 2, when disposed in the retraction position, sensor 22 is disposed on an opposite (upstream) side of the ball valve 14 from process 12. Moreover, in particular embodiments, when in the retraction position, sensor 22 is disposed within retraction chamber 16 as also shown.

Conversely, as shown in FIG. 3, when in the insertion position, sensor 22 extends into ball valve 14, for operative engagement with process 12 (FIG. 1). Moreover, in particular embodiments, at least a portion of sensor 22 extends completely through ball valve 14 and into the path (e.g., as defined by process conduit 13) of process 12, to facilitate such operative engagement.

Operation of embodiments of the invention will now be described. Initially, a suitable sensor 22, such as the above-referenced DolpHin™ Series sensors (Foxboro® Company) is fastened onto sensor sleeve 41 as shown in FIG. 1. Assembly 18 may then be secured to retraction chamber 16 (with actuator 20 and ball valve in the closed position as shown), by inserting sensor end 40 of the tube 24 into chamber 16, and tightening chamber nut 26 thereto. Tube 24 and sensor 22 will be disposed in the retracted position as shown in FIG. 2.

A user may then operate actuator 20 by moving it into its open position, which as shown in FIG. 2, serves to engage guard 50 with fastener 26 as described above. As also discussed above, this operation of actuator 20 serves to open ball valve 14. At this point, tube 24 and sensor 22 may be moved into the insertion position as shown. Since guard 50 does not block access to fastener (tubing nut) 40, nut 40 may be easily tightened to secure tube 24 in this insertion position.

When sensor 22 requires servicing or replacement, the user may simply reverse the above-described operation, by first loosening tubing nut 40 and moving tube 24 into the retraction position of FIG. 2. At this point, actuator 20 will still be in the valve-open position, as shown in phantom in FIG. 2. Advantageously, guard 50 remains in operative engagement with chamber nut 26, to nominally prevent a user from inadvertently loosening chamber nut 26 and withdrawing the sensor 22 without first closing ball valve 14.

The user then moves actuator 20 to its valve-closed position as shown, which in turn, provides access to nut 26. Once in this position, ball valve 14 has safely isolated both retraction chamber 16 and insertion assembly 18 from process 12. A user may then loosen nut 26 and withdraw tube 24 along with sensor 22, either with or without first draining any process fluid via purge ports 17.

In this manner, embodiments of the present invention advantageously increase the safety of sensor insertion assemblies by nominally preventing withdrawal of a sensor without first retracting the sensor and closing the valve.

In the preceding specification, the invention has been described with reference to specific exemplary embodiments thereof. It will be evident that various modifications and changes may be made thereunto without departing from the broader spirit and scope of the invention as set forth in the claims that follow. The specification and drawings are accordingly to be regarded in an illustrative rather than restrictive sense.

The invention claimed is:

1. An interlocked ball valve sensor insertion assembly for use in a manufacturing process comprising:
   a ball valve configured for being couplable to the manufacturing process;
   a retraction chamber coupled to the ball valve;
   the ball valve disposed to alternately couple and decouple the retraction chamber with the process;
   an insertion assembly coupled to the retraction chamber; the insertion assembly including an axially slidable insertion tube;
   the tube having a sensor supportably disposed on an end thereof;
   the tube having a range of motion extending from an insertion position to a retraction position;
   the sensor extending into the ball valve and into operative engagement with the process when in the insertion position;
   the sensor being disposed on an opposite side of the ball valve from the process when in the retraction position;
   a first fastener coupled to the tube, the first fastener configured to selectively permit and prevent movement of the tube within the range of motion;
   a second fastener coupled to the tube, the second fastener configured to selectively permit and prevent removal of the tube from the retraction chamber;
   an actuator coupled to the ball valve;
   the actuator configured to effect the alternate coupling and decoupling;
   the actuator configured for alternate engagement and disengagement with the second fastener;
   the alternate engagement and disengagement respectively inhibiting and enabling operational access to the second fastener;
   wherein the actuator is configured to effectively couple the process fluid with the retraction chamber and to inhibit operational access to the second fastener when the tube is disposed in the insertion position; and
   wherein the actuator is configured to effectively decouple the process fluid from the retraction chamber and to enable operational access to the second fastener when the tube is disposed in the retracted position.

2. An interlocked valve sensor insertion assembly for use in a manufacturing process, the assembly comprising:
   a valve configured for engagement with the manufacturing process;
   a retraction chamber coupled to the valve;
   the valve having a range of motion extending from an open position to a closed position;
   an insertion assembly coupled to the retraction chamber;
   the insertion assembly including a slidable insertion tube;
   the insertion tube having a sensor end configured to support a sensor;

the insertion tube having a range of motion extending from an insertion position to a retraction position;

the range of motion of the insertion tube being configured to extend the sensor into the valve;

a fastener configured to releasably couple the tuba to the retraction chamber;

an actuator configured for engagement with both the valve and the fastener; and the actuator configured to alternately engage and disengage the fastener when the valve is respectively disposed in said open and closed positions.

3. The assembly of claim 2, wherein the valve is configured to alternately couple and decouple the retraction chamber with the process, when respectively disposed in the open and closed positions.

4. The assembly of claim 2, wherein the valve is disposed to interfere with the range of motion of the tube when the valve is disposed in said closed position.

5. The assembly of claim 2, wherein the insertion tube is configured to extend the sensor into the valve when disposed in the insertion position.

6. The assembly of claim 2, wherein the valve is configured to alternately couple and decouple the retraction chamber with the process.

7. The assembly of claim 6, wherein the actuator is configured to effect the alternate coupling and decoupling.

8. The assembly of claim 7, wherein the actuator is configured for alternate engagement and disengagement with the fastener to respectively inhibit and enable operation of the fastener.

9. The assembly of claim 8, wherein the actuator is configured for engagement with the fastener when the valve is disposed in the open position.

10. The assembly of claim 9, wherein the actuator is configured for disengagement with the fastener when the valve is disposed in the closed position.

11. The assembly of claim 2, comprising an other fastener configured to selectively permit and prevent movement of the tube within the range of motion.

12. The assembly of claim 11, wherein the actuator is configured to decouple the process fluid from the retraction chamber, and to enable operational access to the second fastener, when the tube is disposed in the retracted position.

13. The assembly of claim 2, wherein the valve comprises a ball valve.

14. The assembly of claim 2, wherein the retraction chamber comprises at least one purge port.

15. The assembly of claim 2, wherein the actuator comprises handle coupled at a proximal end thereof to the valve.

16. The assembly of claim 15, wherein the actuator comprises a guard disposed at a distal end thereof.

17. The assembly of claim 16, wherein the guard is configured for alternate engagement and disengagement with the fastener.

18. The assembly of claim 17, further comprising a lock operatively engageable with said guard, said lock being disposed to selectively prevent and permit said disengagement.

19. The assembly of claim 17, wherein the engagement comprises disposing the guard in superposed orientation with at least a portion of the fastener.

20. The assembly of claim 19, wherein the fastener includes a nut with a periphery having at least two opposed parallel surfaces, and the guard includes a U-shaped member having portions configured for superposition with the opposed parallel surfaces.

21. A method for providing an interlocked valve sensor insertion assembly for use with a manufacturing process, the method comprising:

(a) providing a valve which is couplable with the manufacturing process, the valve having a range of motion extending from an open position to a closed position;

(b) coupling a retraction chamber to the valve;

(c) coupling an insertion assembly to the retraction chamber;

(d) providing the insertion assembly with an axially slidable insertion tube;

(e) configuring an end of the insertion tube to support a sensor;

(f) configuring the insertion tubs with a range of motion extending from an insertion position to a retraction position, wherein the sensor extends into the valve in the insertion position;

(g) releasably coupling the tube to the insertion assembly with a fastener; and (h) configuring an actuator for selective engagement with both the valve and the fastener, wherein the actuator alternately moves the valve between said open and closed positions, while respectively engaging and disengaging the fastener.

22. An interlocked valve sensor insertion assembly for use in a manufacturing process, the assembly comprising:

a valve configured for engagement with the manufacturing process;

a housing coupled to the valve;

the valve having a range of motion extending from an open position to a closed position;

an insertion member slidable coupled to the housing;

the insertion member having a sensor end configured to support a sensor;

the insertion member having a range of motion extending from an insertion position to a retraction position;

a fastener configured to releasably couple the insertion member to the housing;

an actuator configured for engagement with both the valve and the fastener; and the actuator configured to alternately engage and disengage the fastener when the valve is respectively disposed in said open and closed positions.

23. An interlock for use in a manufacturing process, the interlock comprising:

an actuator configured for engagement with a valve operatively engagable with the manufacturing process;

the valve being coupled to a housing, and having a range of motion extending from an open position to a closed position;

the actuator also being configured for engagement with a fastener configured to releasably couple an insertion member to the housing;

the insertion member having a sensor end configured to support a sensor;

the insertion member having a range of motion extending from an insertion position to a retraction position;

the actuator configured to alternately engage and disengage the fastener when the valve is respectively disposed in said open and closed positions.

* * * * *